US00PP37235P2

(12) United States Plant Patent
Steele

(10) Patent No.: US PP37,235 P2
(45) Date of Patent: Jan. 27, 2026

(54) ***ADIANTUM* PLANT NAMED 'TASSELS'**

(50) Latin Name: *Adiantum hybrida*
Varietal Denomination: TASSELS

(71) Applicant: Wendy Steele, Henderson (AU)

(72) Inventor: Wendy Steele, Henderson (AU)

( * ) Notice: Subject to any disclaimer, the term of this patent is extended or adjusted under 35 U.S.C. 154(b) by 0 days.

(21) Appl. No.: 19/093,595

(22) Filed: Mar. 28, 2025

(51) Int. Cl.
*A01H 5/12* (2018.01)
*A01H 9/00* (2006.01)

(52) U.S. Cl.
USPC ..... Plt./379

(58) Field of Classification Search
USPC ..... Plt./379, 373
See application file for complete search history.

(56) References Cited

U.S. PATENT DOCUMENTS

PP33,715 P2 * 11/2021 Uebelhart ..... A01H 6/14 Plt./437
PP33,733 P2 * 12/2021 Uebelhart ..... A01H 6/14 Plt./286

* cited by examiner

*Primary Examiner* — Karen M Redden

(57) ABSTRACT

A new and distinct *Adiantum* cultivar named 'TASSELS' is disclosed, characterized by unique clusters of pinnae forming at terminus of fronds on mature plants, creating a different ornamental appearance due this this distinct morphology. Fronds are pendulous, large and composed of large pinnae. Plants of the new variety have been observed to recover rapidly and entirely from die back caused by drought. The new variety is a *Adiantum*, typically produced as an ornamental plant.

2 Drawing Sheets

Latin name of the genus and species: *Adiantum hybrida*.
Variety denomination: 'TASSELS'.

BACKGROUND OF THE INVENTION

The new cultivar *Adiantum* 'TASSELS' was discovered by the inventor as a chance seedling growing among a plant collection of various *Adiantum* species in the inventor's home greenhouse in Henderson, Auckland, New Zealand. The exact parentage cannot be identified. The inventor is a collector of ferns and first identified the interesting seedling growing under a bench in her home greenhouse in 1985.

'TASSELS' was first asexually reproduced by the inventor at this home greenhouse in Henderson, Auckland, New Zealand. and has been found to retain its distinctive characteristics through 5 generations of asexual propagation.

SUMMARY OF THE INVENTION

The following are the most outstanding and distinguishing characteristics of the new cultivar when grown under normal horticultural practices:

1. Unique clusters of pinnae forming at terminus of fronds on mature plants, creating a different ornamental appearance due to this distinct morphology.
2. Large pinnae.
3. Pendulous fronds.
4. Large bipinnate fronds.

COMPARISON WITH PARENT VARIETIES

The seed and pollen parents are unknown.

COMPARISON WITH COMMERCIAL CULTIVARS

'TASSELS' can be compared to the unnamed, unpatented species *Adiantum excisum*. Plants are similar in most horticultural characteristics, however, 'TASSELS' differs in the following:

1. The new variety forms pendulous fronds; this comparator forms horizontal or arching fronds.
2. The new variety forms clusters of pinnae on terminal ends of fronds of mature plants. This comparator has fronds composed of evenly distributed pinnae.

'TASSELS' can be compared to the unnamed, unpatented species *Adiantum fragrans*. Plants are similar in most horticultural characteristics, however, 'TASSELS' differs in the following:

1. The new variety forms pendulous fronds; this comparator forms horizontal fronds.
2. The new variety forms clusters of pinnae on terminal ends of fronds of mature plants. This comparator has flat fronds composed of evenly distributed pinnae on a horizontal plane.

'TASSELS' can be compared to the unnamed, unpatented species *Adiantum capillus-veneris* commonly available. Plants of the two varieties are similar in most horticultural characteristics, however, 'TASSELS' differs in the following:

1. Fronds of the new variety are larger than fronds of this comparator.
2. Pinnae of the new variety are larger than fronds of this comparator.
3. The new variety forms clusters of pinnae on terminal ends of fronds of mature plants.

4. The new variety forms pendulous fronds; this comparator forms arching fronds.

BRIEF DESCRIPTION OF THE PHOTOGRAPHS

The present invention of a new and distinct variety of *Adiantum* is shown in the accompanying photographs, the colors being as nearly true as possible with color photographs of this type.

DETAILED BOTANICAL DESCRIPTION

Figure 1:
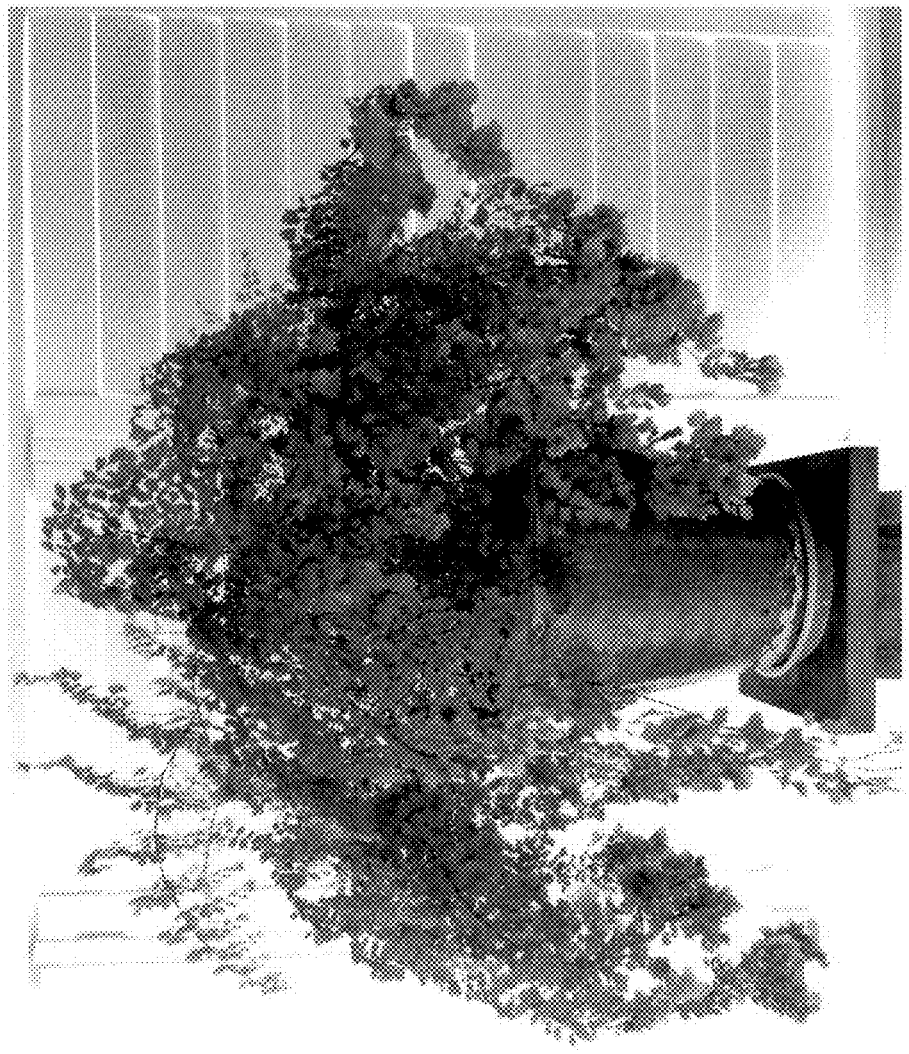
FIG. 1 illustrates a plant of approximately 24 months from a division.
Figure 2:
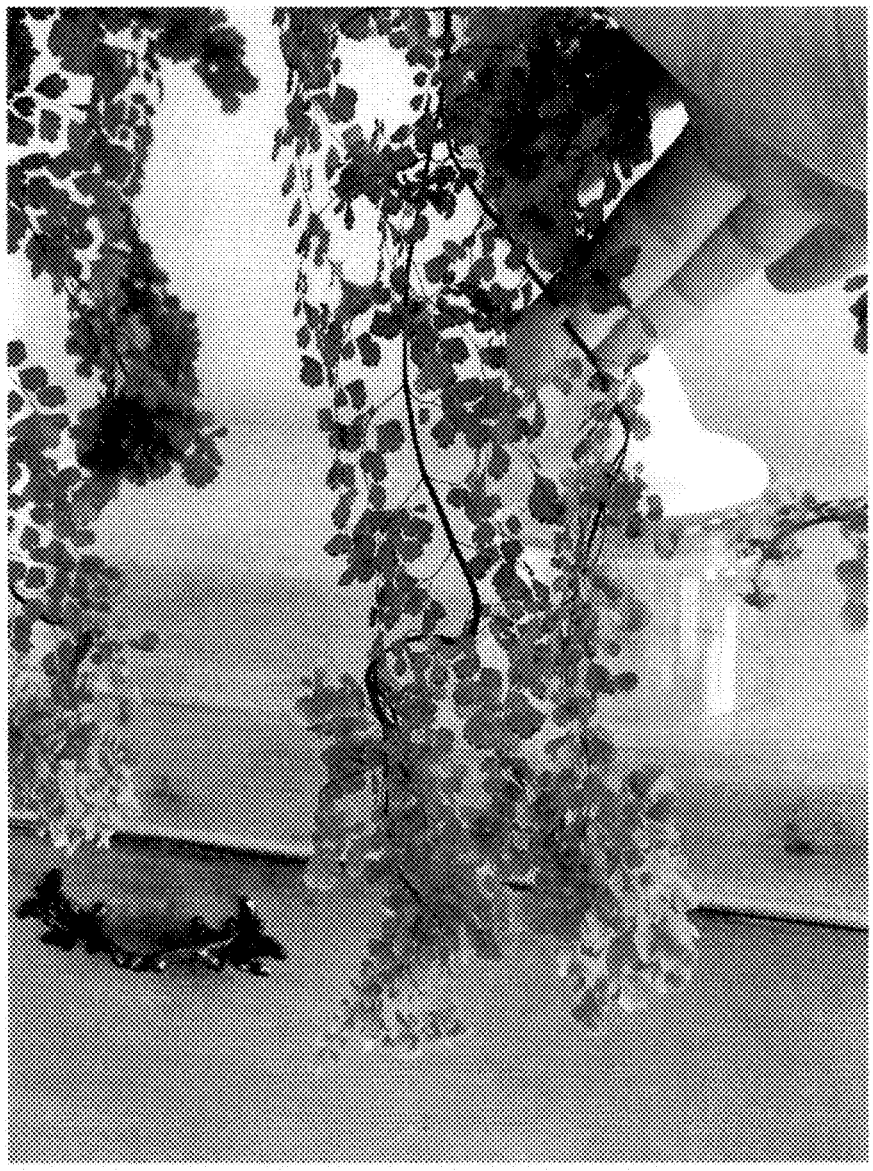
FIG. 2 illustrates a close up of the frond, including the clustered terminal pinnae.

In the following description, color references are made to The Royal Horticultural Society Color Chart, 2015 edition, except where general terms of ordinary dictionary significance are used. The following observations and measurements describe 'TASSELS' plants grown outdoors in Henderson, Auckland, New Zealand. Temperatures ranged from about 2° C. to 32° C. No artificial light, photoperiodic treatments or chemical treatments were given to the plants. Measurements and numerical values represent averages of typical plant types.

Botanical classification: *Adiantum hybrida* 'TASSELS'.

PROPAGATION

Typical method: Division or tissue culture.

PLANT

Plant type: Fern.
Growth habit: Pendulous.
Height: About 15 to 20 cm from the soil level to the uppermost foliage. From the lowest foliage to the top foliage about 45 to 55 cm.
Plant spread: 30 cm.
Growth rate: Moderate.
Root description: Fibrous, Brown N199B.

FOLIAGE

Frond:
- *Quantity per plant*.—Average 30 to 60.
- *Frond type*.—Pinnate.
- *Overall frond shape*.—Lanceolate. Mature fronds have an ovate cluster of pinnae at the terminal end.
- *Overall frond aspect*.—Pendulous.
- *Average frond length* (*including stipe*).—25 to 60 cm.
- *Average frond width*.—8 to 12 cm.
- *Pinnae per frond*.—Average range 80 to 140.

Pinnae/leaflets:
- *Average length*.—8 to 18 mm.
- *Average width*.—7 to 15 mm.
- *Pinna shape*.—Somewhat irregular cordate.
- *Apex*.—Rounded, often with a deep notch forming 2 irregular lobes.
- *Base*.—Broad attenuate.
- *Margin*.—Irregularly notched.
- *Aspect*.—Flat.
- *Texture of top surface*.—Glabrous.
- *Texture of bottom surface*.—Glabrous.
- *Appearance of top surface*.—Matte.
- *Appearance of bottom surface*.—Matte.
- *Color*.—Young Upper Surface: Yellow-Green 145C flushed 144C. Young Lower Surface: Yellow-Green 145C flushed 144C. Mature Upper Surface: Green 143C flushed 143B. Mature Lower Surface: Green 143C flushed 143B.

Venation: Indistinguishable from leaflet blade.

Stipe:
- *Length*.—Average range 1 to 3 cm.
- *Width*.—About 5 mm.
- *Shape*.—Rounded.
- *Strength*.—Moderately strong to strong.
- *Texture*.—Scaled.
- *Color*.—RHS Greyed-Orange 167A and 177A and 177B.

Pinna petiole (if present):
- *Length*.—Average range 4 to 9 mm.
- *Width*.—About 1 mm.
- *Texture*.—Glabrous.
- *Color*.—RHS Green 143C flushed Greyed-Orange 167A.

Costa/pinna midrib: Not present.

Rachis description:
- *Length*.—Average range 10 to 40 cm.
- *Width*.—About 4 mm.
- *Color*.—RHS Greyed-Orange 177A heavily flushed Greyed-Purple 187B.
- *Texture*.—Glabrous.
- *Strength*.—Moderate.

OTHER CHARACTERISTICS

Disease and pest resistance: Neither resistance nor susceptibility to additional normal diseases and pests of *Adiantum* has been observed.

Drought tolerance: Excellent recovery from extreme drought observed. A plant appearing dead from lack of water, was cut back to the base and resumed active growth within 1 month and complete recovery within 2 months of the cutback.

Sori: Wedge-shaped, occurring along leaf apex. 3 mm long and 2 mm in diameter. Colored near Brown 200A.

What is claimed is:

1. A new and distinct cultivar of *Adiantum* plant named 'Tassels' as herein illustrated and described.

* * * * *